United States Patent [19]

Ichijima et al.

[11] 4,366,237

[45] Dec. 28, 1982

[54] SILVER HALIDE COLOR PHOTOGRAPHIC LIGHT-SENSITIVE MATERIAL

[75] Inventors: Seiji Ichijima; Keiichi Adachi; Tadashi Ogawa, all of Minami-ashigara, Japan

[73] Assignee: Fuji Photo Film Co., Ltd., Kanagawa, Japan

[21] Appl. No.: 280,603

[22] Filed: Jul. 6, 1981

[30] Foreign Application Priority Data

Jul. 4, 1980 [JP] Japan .................................. 55-91570

[51] Int. Cl.³ .................................................. G03C 1/40
[52] U.S. Cl. ...................................... 430/505; 430/554; 430/555; 430/558
[58] Field of Search ........................ 430/554, 555, 505

[56] References Cited

U.S. PATENT DOCUMENTS

| | | | |
|---|---|---|---|
| 3,325,482 | 6/1967 | Monbaliu et al. | 430/554 |
| 3,370,952 | 2/1968 | Dawson | 430/554 |
| 3,468,665 | 9/1969 | Misu et al. | 430/554 |
| 3,615,505 | 10/1971 | Van Poucke et al. | 430/554 |
| 4,128,427 | 12/1978 | Monbaliu et al. | 430/554 |
| 4,254,213 | 3/1981 | Masuda et al. | 430/555 |
| 4,301,235 | 11/1981 | Ichijima et al. | 430/555 |

*Primary Examiner*—J. Travis Brown
*Attorney, Agent, or Firm*—Sughrue, Mion, Zinn, Macpeak & Seas

[57] ABSTRACT

A silver halide color photographic light-sensitive material is described comprising a support having thereon at least one silver halide emulsion layer, said photographic material containing a 5-pyrazolone magenta coupler substituted with a tertiary alkanamido group at the 3-position thereof.

16 Claims, No Drawings

4,366,237

SILVER HALIDE COLOR PHOTOGRAPHIC LIGHT-SENSITIVE MATERIAL

FIELD OF THE INVENTION

The present invention relates to silver halide photographic light-sensitive materials containing a novel magenta color forming coupler.

BACKGROUND OF THE INVENTION

Upon color development of an exposed silver halide photographic light-sensitive material, an oxidized aromatic primary amine developing agent reacts with a coupler to form a dye, with a dye image thus being formed. In this system, color reproduction is usually carried out using a subtractive method, and in order to reproduce blue, green and red color, yellow, magenta and cyan color images which are in a complementary relation thereto, respectively, are formed. In general, pyrazolone, cyanoacetyl or indazolone type couplers are used for the formation of magenta color images.

In one of the most preferred embodiments of color photographic light-sensitive materials, dye image-forming couplers are added to silver halide emulsions. Couplers added to emulsions must be rendered nondiffusible (or diffusion-resistant) in a binder matrix of the emulsions.

Most well-known conventional magenta color image-forming couplers are 4-equivalent couplers. However, various kinds of 2-equivalent couplers are also known, as described in various patents. Since 2-equivalent couplers require only one half the silver halide as compared with ordinary 4-equivalent couplers to form a dye, their use enables rapid processing of light-sensitive materials due to the thinness of the light-sensitive layers, and the photographic properties are improved due to a reduction in film thickness, and the economic advantages are achieved.

Various 5-pyrazolone type couplers are known for forming magenta color images. For instance, as the substituents at the 3-position of the 5-pyrazolone ring, an alkyl group, an aryl group, an alkoxy group as described in U.S. Pat. No. 2,439,098, a ureido group as described in U.S. Pat. No. 3,558,319, an anilino group as described in U.S. Pat. No. 2,311,081 (U.S. Pat. Re. No. 22,329), a dialkylamino group as described in U.S. Pat. No. 3,615,506, and an acylamino group, are known.

3-Acylamino-5-pyrazolone type couplers are frequently described, as in U.S. Pat. Nos. 2,369,489, 2,600,788, etc. However, few attempts have been known to improve this type of couplers by modifying the acylamino group.

For instance, the 3-position of the 5-pyrazolone ring can be substituted with a benzamido group, an acetamido group, a straight chain alkanamido group, a phenylacetamido group, a phenoxyacetamido group, or a naphthamido group as described in U.S. Pat. No. 2,369,489, or can be substituted with a benzamido group, an acetamido group, a phenylacetamido group or a phenoxyalkanamido group as described in U.S. Pat. No. 2,600,788. Also, the 3-position of the 5-pyrazolone ring substituted with a secondary branched alkanamido group is described in Japanese patent publication No. 16058/74.

The compounds described in these references exhibit fairly good color forming properties. However, these compounds have the disadvantage that they require a large amount of a coupler solvent which must be used for the incorporation of the couplers into an emulsion due to the poor solubility thereof in the organic solvent, and as a result it is difficult to reduce the thickness of the layer containing the couplers. Thus, improvement in the sharpness of the images formed cannot be adequately achieved, and the amount of the coupler solvent cannot be reduced, since the color forming property thereof is influenced by any change in the amount of solvent used.

The couplers according to the present invention are considerably improved couplers which have few of the disadvantage as described above with respect to the fundamental properties required for use in photographic light-sensitive materials.

SUMMARY OF THE INVENTION

An object of the present invention is to provide a color photographic light-sensitive material in which the amount of coupler solvent in a photographic emulsion layer containing couplers is reduced by using a novel magenta color image forming coupler therein, thus improving the sharpness of color images obtained.

Another object of the present invention is to provide a color photographic light-sensitive material of high sensitivity by using a novel magenta coupler.

A further object of the present invention is to provide a color photographic light-sensitive material in which the color forming efficiency is improved, the amount of coupler used is reduced and the amount of silver halide used is also reduced.

A still further object of the present invention is to provide a novel magenta coupler which can be synthesized with ease and in high yield.

A still further object of the present invention is to provide a coupler which has excellent solubility in an organic solvent and is suitable for use in an oil solution system in which the coupler is dispersed in an aqueous medium as a fine colloid particle, and then the dispersion is added to an emulsion.

Other objects of the present invention will become apparent from the following detailed description and examples.

These objects of the present invention can be effectively attained by incorporating a 3-acylamino-5-pyrazolone type coupler wherein the acylamino group is a tertiary alkanamido group as a magenta color image forming coupler into a silver halide photographic emulsion layer of a color photographic light-sensitive material.

DETAILED DESCRIPTION OF THE INVENTION

In preferred magenta couplers according to the present invention, the 1-position of the pyrazolone nucleus is substituted with a hydrophobic residue and the 4-position of the pyrazolone nucleus may be hydrogen or may be substituted with a coupling releasable group. The term "coupling releasable group" as used in this specification has the conventional meaning as used in the field of color forming couplers. That is, the term means a group which is released from the coupler by the reaction of the oxidation product of an aromatic primary amine developing agent and the coupler.

The substituents on the 1-position and the 3-position of the 5-pyrazolone compound according to the present invention have a hydrophobic property in a degree sufficient for insolubilizing the dye formed therefrom, and must not contain a water solubilizing group. The term "water solubilizing group" as used herein means a group which imparts a hydrophilic property sufficient for solubilizing the dye formed therefrom in an aqueous medium. Examples of the water solubilizing group are a sulfo group, an oxysulfo group and a carboxy group. When such a water solubilizing group is introduced in the 1-position and/or the 3-position of the 5-pyrazolone, the azomethine dye formed therefrom is soluble to an aqueous medium and a sufficient amount of the dye for forming color images cannot be maintained in the emulsion layer. Therefore, couplers having a water soluble pyrazolone nucleus are not suitable for the purposes of the present invention.

5-Pyrazolone couplers useful in the present invention can be represented by formula (I):

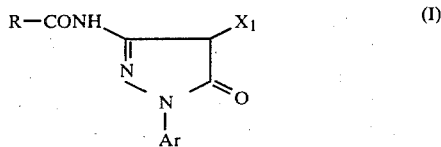

wherein R represents a tertiary alkyl group having from 4 to 30 carbon atoms, and preferably from 4 to 18 carbon atoms, which may be substituted, and includes a cyclic alkyl group; Ar represents a phenyl group which may be substituted with one or more substituents selected from a halogen atom, an alkyl group, an alkoxy group and an acylamino group; and $X_1$ represents hydrogen or a coupling releasable group.

Examples of the tertiary alkyl groups for R include a tert-butyl group, a tert-pentyl group, a 1,1-dimethyldecyl group, an adamantyl group, a norbornan-1-yl group, a 1,1-dimethyloctadecyl group, etc.

Ar in formula (I) represents in more detail a phenyl group which may be substituted with one or more substituents selected from a halogen atom (for example, a fluorine atom, a chlorine atom, a bromine atom), a straight chain or branched chain alkyl group having from 1 to 35 carbon atoms, and preferably from 1 to 22 carbon atoms, an alkoxy group containing a straight chain or branched chain alkyl group having from 1 to 35 carbon atoms, and preferably from 1 to 22 carbon atoms, or an acylamino group containing a straight chain or branched chain alkyl group having from 1 to 35 carbon atoms, and preferably from 1 to 22 carbon atoms, and the acylamino group may be further substituted with an aryloxy group.

$X_1$ in formula (I) represents hydrogen or a coupling releasable group. Examples of the coupling releasable group include a thiocyano group, an acyloxy group (for example, an acetoxy group, a dodecanoyloxy group, an octadecanoyloxy group, a 3-pentadecylphenoxyacetoxy group, a benzoyloxy group, a β-naphthoyloxy group, a 3-[γ-(2,4-di-tert-amylphenoxy)butyramido]benzoyloxy group, etc.), an aryloxy group (for example, a phenoxy group, a p-chlorophenoxy group, a p-nitrophenoxy group, a naphthoxy group, etc.), an alkoxy group, a halogen atom (for example, a chlorine atom, a fluorine atom, etc.), an arylazo group (for example, a phenylazo group, a naphthylazo group, etc.), an aryltriazolyl group (for example, a 1-benzotriazolyl group, a 2-benzotriazolyl group, a 2-naphthotriazolyl group, etc.), an alkylthio group (for example, a dodecylthio group, a hexadecylthio group, etc.), an arylthio group (for example, a phenylthio group, a naphthylthio group, etc.), a heterocyclic thio group (for example, a 2-benzo-thiazolylthio group, a 1-phenyl-5-tetrazolylthio group, a 2-benzoxazolylthio group, a 2-benzimidazolylthio group, a 5-phenyl-1,3,4-oxadiazolyl-2-thio group, etc.), a cycloalkylthio group (for example, a cyclohexylthio group, etc.), a cycloalkoxy group (for example, a cyclohexyloxy group, etc.), an imido group (for example, a phthalimido group, a succinimido group, a 5,5-dimethyl-3-hydantoinyl group, a 5,5-dimethyl-3-oxazolidinyl group, etc.), an imidazolyl group (for example, a 1-imidazolyl group, a 2-methyl-1-imidazolyl group, a 1-benzimidazolyl group, etc.), a triazolyl group (for example, a 3,5-diethyl-1,2,4-triazol-1-yl group, etc.), an acylamino group (for example, a benzamido group, an acetylamino group, etc.), a sulfonamido group (for example, a benzenesulfonamido group, a methanesulfonamido group, etc.), a cycloamino group (for example, a piperidino group, a morpholino group, etc.), a pyrazolyl group (for example, a 4-chloro-1-pyrazolyl group, a 3-dodecyl-1-pyrazolyl group, etc.), and an indazolyl group (for example, a 6-tetradecanamido-1-indazolyl group, etc.), and the like.

The magenta color forming couplers represented by above-described formula (I) are novel compounds.

Of the magenta color forming couplers used in the present invention, those represented by the following formulae (II) and (III) are particularly preferred.

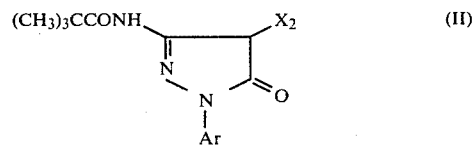

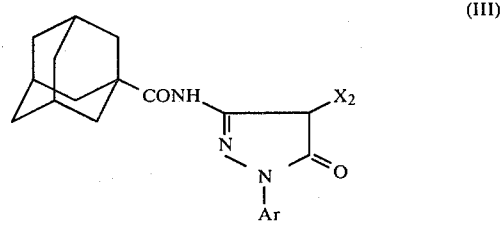

In formulae (II) and (III), Ar has the same meaning as defined for formula (I); $X_2$ represents a substituted or unsubstituted alkylthio group or aralkylthio group having from 2 to 30 carbon atoms, and preferably from 10 to 20 carbon atoms (for example, a 2-ethylhexylthio group, a dodecylthio group, a hexadecylthio group, a 3-(4-phenylphenoxy)propylthio group, a phenoxypropylthio group, a 3-(4-tert-pentylphenoxy)-propylthio group, a phenylpropylthio group, a 2-(2,4-di-tert-amylphenoxy)ethylthio group, etc.), or a substituted or unsubstituted arylthio group having from 6 to 30 carbon atoms, and preferably from 10 to 20 carbon atoms (for example, a 4-dodecylphenylthio group, a 4-tetradecyloxyphenylthio group, a 3-pentadecylphenylthio group, a 3-dodecylcarbamoylphenylthio group, etc.).

The couplers represented by formulae (II) and (III) have the advantages that since they have a particularly high color forming efficiency, the amount of the couplers used in a color photographic material can be reduced compared to conventional couplers, and they show less tendency to changes in the color density obtained when the amount of the coupler dispersing oil is varied.

In order to render the couplers diffusion-resistant, a group having a hydrophobic moiety containing from 8 to 32 carbon atoms is introduced into the coupler molecule. Such a moiety is called a ballasting group. This ballasting group can be connected to the coupler skeletal structure directly or through an ether bond, a carbonamido bond, a sulfonamido bond, a ureido bond, an ester bond, an imido bond, a carbamoyl bond, a sulfamoyl bond, or the like.

Several specific examples of the ballasting group are as described in the specific examples of the couplers of the present invention.

Typical examples of the ballasting groups include, e.g., an alkyl group, an alkoxyalkyl group, an alkenyl group, an aryl group substituted by an alkyl group, an aryl group substituted by an alkoxy group, a terphenyl group, and the like. These ballasting groups may be substituted by, for example, a halogen atom (e.g., fluorine, chlorine, etc.), a nitro group, a cyano group, an alkoxycarbonyl group, an amido group, a carbamoyl group, a sulfonamido group, etc. Specific examples of the ballasting group include an n-octyl group, a 2-ethylhexyl group, a tert-octyl group, an n-nonyl group, an n-decyl group, an n-dodecyl group, a 1,1-dimethyldecyl group, a 2,2-dimethyldecyl group, an n-octadecyl group, a 2-(n-hexyl)decyl group, an n-octadecyl group, a 9,10-dichlorooctadecyl group, a heptyloxyethyl group, a 2,4-di-tert-amylcyclohexyldodecyloxypropyl group, an oleyl group, a 2,4-di-tert-butylphenyl group, a 2,4-di-tertamylphenyl group, a 2,4-di-tert-amyl-6-chlorophenyl group, a 3-n-pentadecylphenyl group, a 2-dodecyloxyphenyl group, a 3-heptadecyloxyphenyl group, an o-terphenyl group, a perfluoroheptyl group, etc.

Examples of couplers according to the present invention include the following compounds, but the present invention is not to be construed as being limited to these couplers.

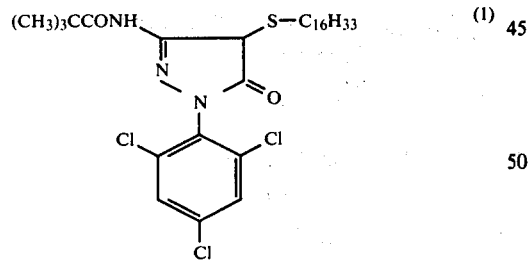
(1)

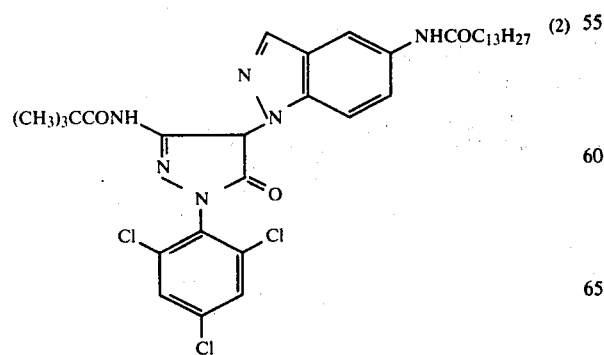
(2)

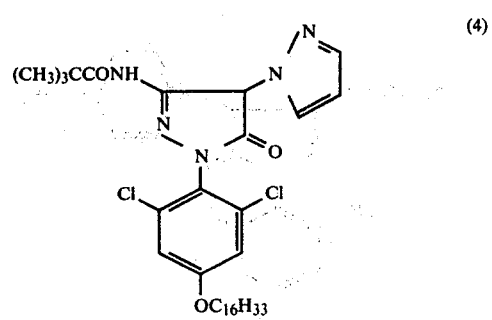
(3)

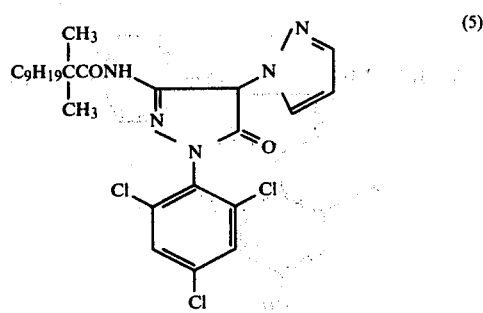
(4)

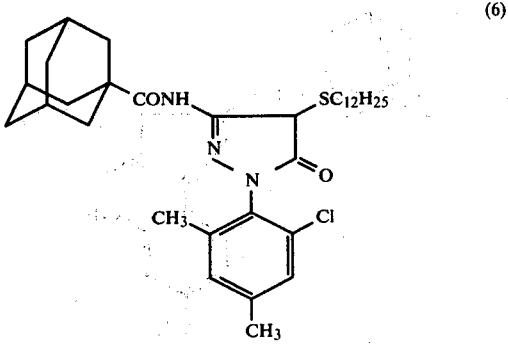
(5)

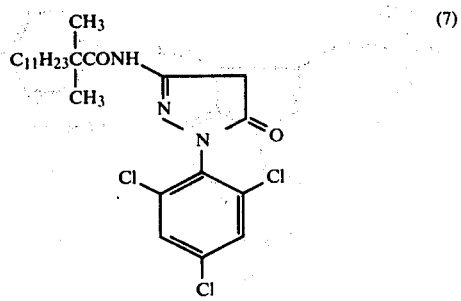
(6)

(7)

-continued
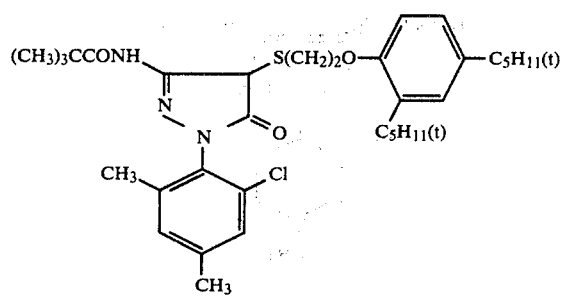
(8)
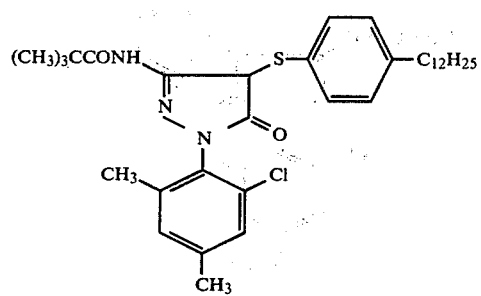
(9)
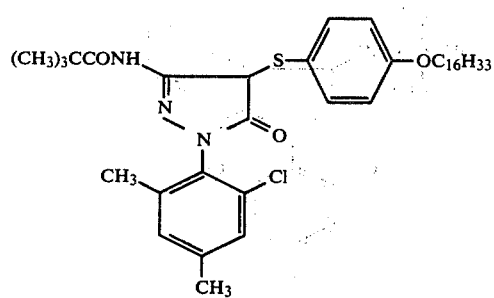
(10)
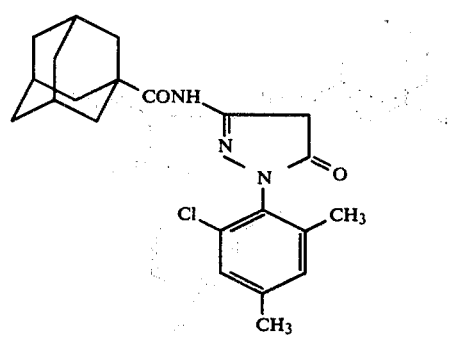
(11)
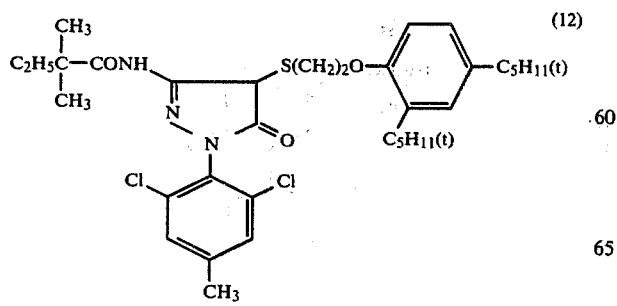
(12)
-continued
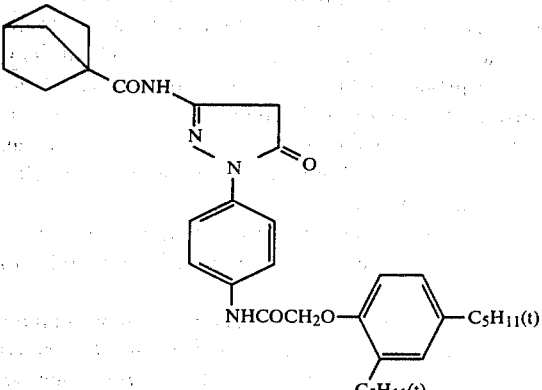
(13)
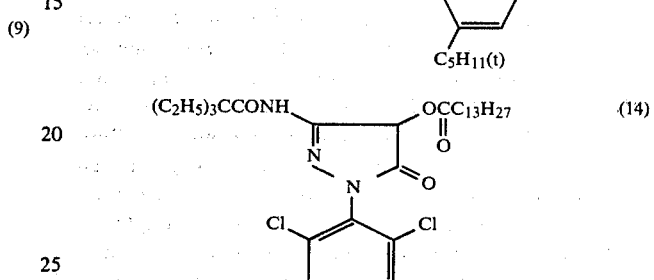
(14)
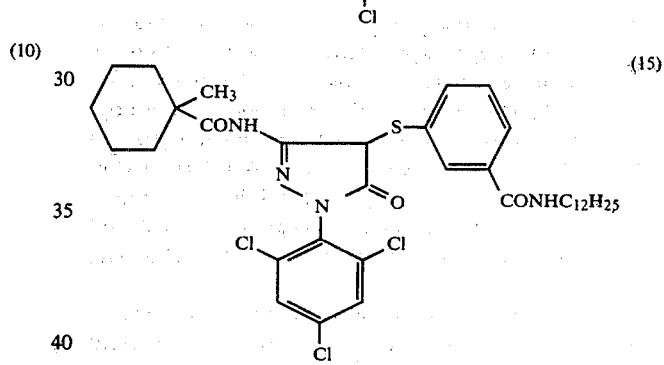
(15)
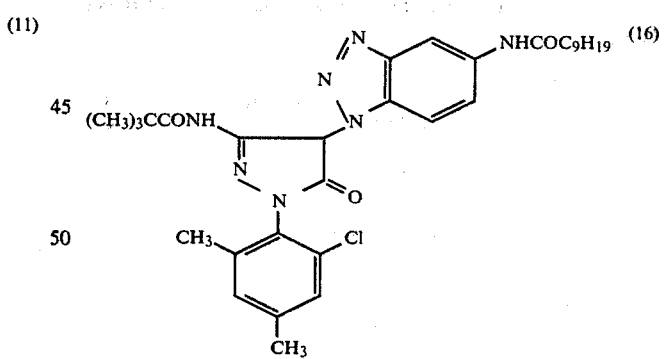
(16)
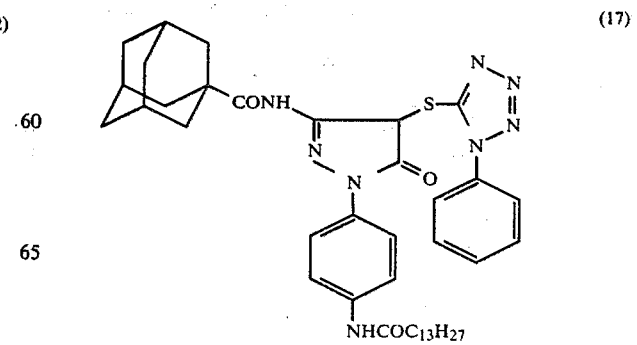
(17)

-continued
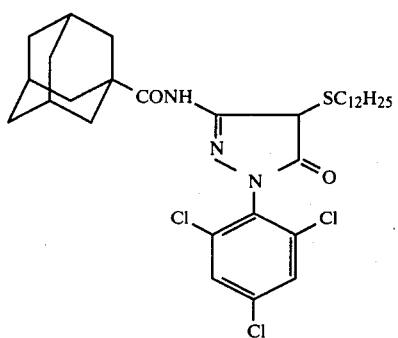 (18)
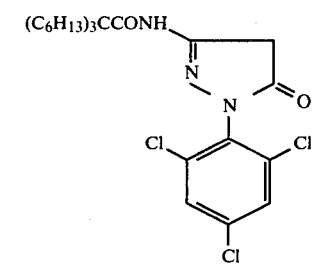 (19)
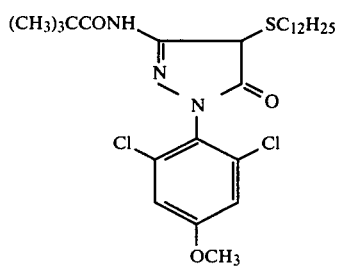 (20)
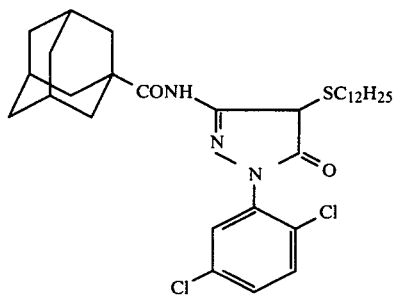 (21)
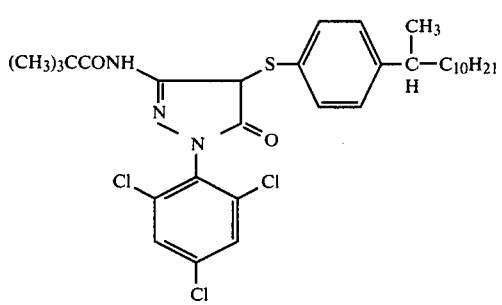 (22)
-continued
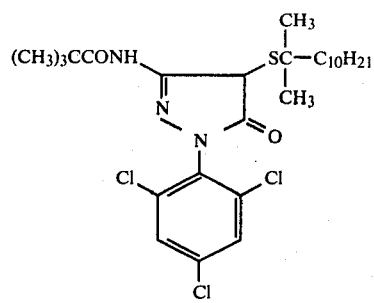 (23)
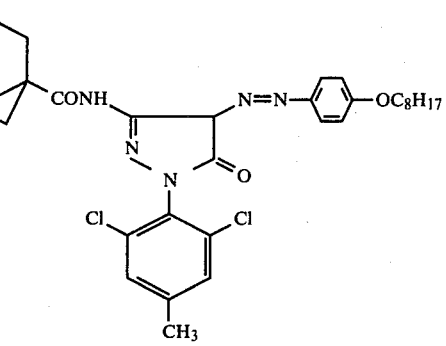 (24)
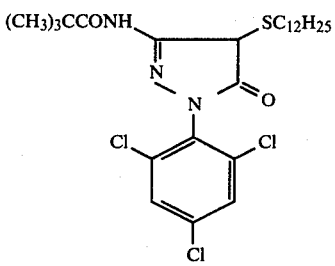 (25)
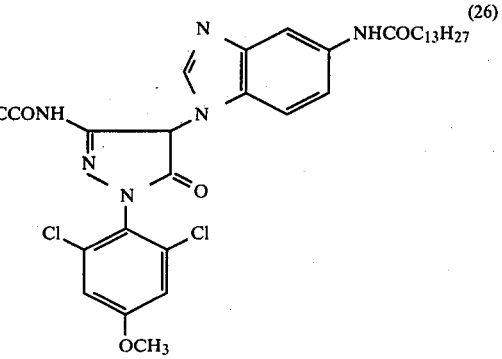 (26)
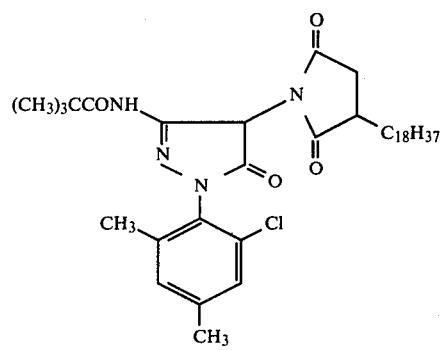 (27)

-continued

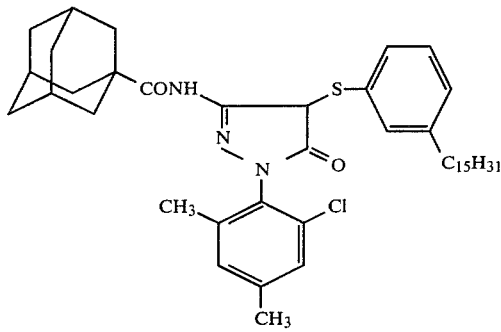
(28)

The couplers according to the present invention can be synthesized with ease by a condensation reaction of a 3-amino-5-pyrazolone with an alkanoyl chloride. In order to obtain a 2-equivalent coupler from a corresponding 4-equivalent coupler, known methods as described, for example, in U.S. Pat. Nos. 3,926,631, 4,040,835, 3,227,554, 3,311,476 and 3,419,391, West German patent application (OLS) No. 2,536,191, Japanese patent application (OPI) Nos. 25056/80 and 29805/80 (the term "OPI" as used herein refers to a "published unexamined Japanese patent application"), etc., can be used.

Typical examples of the synthesis of the photographic couplers of the present invention are described below.

SYNTHESIS EXAMPLE 1

Synthesis of Coupler (11):

23.7 g of 3-amino-1-(2-chloro-4,6-dimethylphenyl)-5-pyrazolone was dissolved in 200 ml of acetonitrile and refluxed with heating. To the solution, an acetonitrile solution containing 19.8 g of 1-adamantane carbonic acid chloride was added dropwise with stirring. After reaction for 3 hours, acetonitrile was removed by distillation. The residue was recrystallized from a solvent mixture of acetonitrile and water to obtain 23 g of the desired compound. The melting point of the compound was 250° to 252° C.

SYNTHESIS EXAMPLE 2

Synthesis of Coupler (6):

22.5 g of the compound obtained in Synthesis Example 1 was added to a mixture of 100 ml of dimethylformamide and 6.8 g of triethylamine and dissolved. To the solution, a solution containing 17.5 g of S-dodecylthioisothiourea hydrochloride dissolved in 50 ml of methanol was added dropwise with stirring. After the completion of the addition, the mixture was heated at 50° C. for 2 hours with stirring. The reaction mixture was poured into 200 ml of water and extracted with ethyl acetate, followed by washing with water. Ethyl acetate was removed by distillation to obtain raw product which was recrystallized from a solvent mixture of acetonitrile and water to obtain 23.5 g of the desired compound. The melting point of the compound was 120° to 121° C.

SYNTHESIS EXAMPLE 3

Synthesis of Coupler (9):

28 g of 4-dodecylthiophenyl was dissolved in 120 ml of dichloromethane and thereto 15 g of sulfuryl chloride was added dropwise at room temperature (25° C.). The mixture was stirred for 2 hours at room temperature and dichloromethane was removed by distillation under reduced pressure. To the residue, 70 ml of dichloromethane and 29 g of 1-(2-chloro-4,6-dimethylphenyl)-3-(2,2-dimethylpropanamido)-5-pyrazolone were added and the mixture was stirred for 10 hours at room temperature. Dichloromethane was removed by distillation under reduced pressure and the residue was crystallized using a solvent mixture of ethyl acetate and hexane to obtain 23 g of the desired coupler. The melting point of the coupler was 118° to 130° C.

SYNTHESIS EXAMPLE 4

Synthesis of Coupler (3):

20 g of 1-(2-chloro-4,6-dimethylphenyl)-3-(2,2-dimethylpropanamido)-5-pyrazolone was dissolved in 100 ml of 80% ethanol (ethanol:water=4:1 in volume ratio) and 5.4 g of potassium carbonate was added thereto. The solution was heated at 80° C., and thereto a solution containing 19.4 g of S-dodecylthioisothiourea hydrochloride dissolved in 100 ml of ethanol was added dropwise with stirring. The mixture was further stirred at 80° C. for 30 minutes with heating. After cooling the mixture to room temperature, the mixture was poured into 1 liter of water and extracted with 1 liter of ethyl acetate. The oil layer was separated and washed with 1 liter of 1 N diluted hydrochloric acid, and then twice with 1 liter portions of water. The oil layer was dried with anhydrous sodium sulfate and concentrated under reduced pressure. Upon recrystallization of the residue from acetonitrile 21 g of the desired coupler was obtained. The melting point of the coupler was 108° to 110° C.

The coupler of the present invention can advantageously be mixed with a solvent dispersion by dissolving the coupler in a water-immiscible organic solvent having a melting point of about 170° C. or higher, a low-boiling organic solvent or a water-soluble organic solvent, or in a high-boiling, water-immiscible organic solvent and/or a low-boiling and/or water-soluble organic solvent.

Any of the high-boiling, water-immiscible organic solvents described in U.S. Pat. No. 2,322,027 can be used as a solvent. Preferred solvents include di-n-butyl phthalate, benzyl phthalate, triphenyl phosphate, tri-o-cresyl phosphate, diphenyl mono-p-t-butylphenyl phosphate, monophenyl di-o-chlorophenyl phosphate, tris(2-ethylhexyl)phosphate, dioctyl phthalate, dibutyl sebacate, acetyl tributyl citrate, tri-t-octyl trimellitate, n-nonylphenol, dioctylbutyl phosphate, N,N-diethyl-laurylamide, trihexyl phosphate, 3-pentadecylphenyl ethyl ether, 2,5-di-sec-amyl-phenyl butyl ether, etc.

Low-boiling organic solvents (having a boiling point of not higher than about 170° C.) or water-soluble organic solvents usable together with or in place of the high-boiling solvents are described in U.S. Pat. Nos. 2,801,171, 2,801,170, 2,949,360, etc. Examples of these organic solvents include the following solvents.

(1) Low-boiling, substantially water-insoluble organic solvents such as methyl acetate, ethyl acetate, propyl acetate, butyl acetate, isopropyl acetate, ethyl propionate, cyclohexanone, sec-butyl alcohol, ethyl formate, butyl formate, nitromethane, nitroethane, carbon tetrachloride, chloroform, etc.

(2) Water-soluble organic solvents such as methyl isobutyl ketone, β-ethoxyethyl acetate, β-ethoxyethyl acetate, tetrahydrofurfuryl adipate, Carbitol acetate (diethylene glycol monoacetate), methoxytriglycol acetate, methyl Cellosolve acetate, acetylacetone, diacetonealcohol, butyl Carbitol, butyl Cellosolve, methyl Carbitol, methyl ethyl ketone, methanol, ethanol, acetonitrile, dimethylformamide, dioxane, etc.

The couplers in accordance with the present invention can be employed in light-sensitive materials containing a reduced amount of silver halide, i.e., about several tenths to about 1/100 as much as the amount in ordinary color light-sensitive materials. With color light-sensitive materials containing a reduced amount of silver halide, suitable color images can be obtained by, for example, halogenation-bleaching silver deposits formed by color development and again conducting color development to increase the amount of dye produced (for example, U.S. Pat. Nos. 2,623,822, 2,814,565, etc.), or by employing a development processing utilizing color intensification using peroxides or cobalt complex salts to increase the amount of dye produced (for example, West German patent application (OLS) No. 2,357,694, U.S. Pat. Nos. 3,674,490, 3,761,265, West German patent application (OLS) Nos. 2,044,833, 2,056,359, 2,056,360, 2,226,770, Japanese patent application (OPI) Nos. 9728/73 and 9729/73, etc.).

The magenta coupler of this invention can be used together with other magenta couplers, as described, for instance, in U.S. Pat. Nos. 2,439,098, 2,369,489, 2,600,788, 3,558,319, 2,311,081, 3,419,391, 3,214,437, 3,006,759, 2,725,292, 3,408,194, 2,908,573, 3,519,429, 3,615,506, 3,432,521, 3,152,896, 3,062,653, 3,582,322, 2,801,171, 3,311,476, British Pat. No. 956,261, Japanese patent publication Nos. 2016/67 and 19032/71, Japanese patent application (OPI) Nos. 74027/74, 13041/75, 131448/74, 21454/73, 60233/75, and 74028/74, with the magenta-colored couplers, as described in U.S. Pat. Nos. 2,983,608, 2,455,170, 2,725,292, 3,005,712, 3,519,429, and 2,688,539, British Pat. Nos. 800,262 and 1,044,778, and Belgian Pat. No. 676,691. They can also be used with the so-called development inhibitor releasing type couplers capable of imagewise releasing development inhibiting compounds at development, such as, for instance, the monothio type couplers as described in U.S. Pat. Nos. 3,227,550, 3,958,993, 3,227,554, 3,938,996 and 4,010,035 and British Pat. No. 953,454, the o-aminophenylazo type couplers as described in U.S. Pat. No. 3,148,062, and the couplers as described in Japanese Patent Publication No. 8750/72 and German patent application (OLS) Nos. 2,414,006, 2,655,871 and 2,163,811, and also with the hydroquinone releasing development inhibiting compounds as described in U.S. Pat. No. 3,297,445 and British Pat. No. 1,058,606.

One or more of the above-described couplers and the like can be employed in the same layer to achieve the properties required for light-sensitive materials and the same compound can be incorporated in two or more different layers. In general, the couplers according to this invention are coated at a coverage of from about $1 \times 10^{-4}$ to $5 \times 10^{-3}$ mol/m$^2$, and preferably from $3 \times 10^{-4}$ to $2 \times 10^{-3}$ mol/m$^2$.

The light-sensitive material of the present invention advantageously contains a p-substituted phenol derivative in an emulsion layer or an adjacent layer for the purpose of improving the light fastness of the magenta dye formed or of preventing yellowing or printout of a coupler remaining in the unexposed areas, color fogging, or the like. Particularly effective p-substituted phenol derivatives are the hydroquinone derivatives described in U.S. Pat. Nos. 2,360,290, 2,418,613, 2,675,314, 2,701,197, 2,704,713, 2,710,801, 2,728,659, 2,732,300, 2,735,765, 2,816,038; the gallic acid derivatives as described in U.S. Pat. Nos. 3,457,079, 3,069,262 and Japanese Patent Publication No. 13496/68; the p-alkoxyphenol derivatives as described in U.S. Pat. No. 2,735,765 and Japanese Patent Application (OPI) No. 4738/72; and p-hydroxyphenol derivatives as described in U.S. Pat. Nos. 3,342,300, 3,573,050, 3,574,627 and Japanese patent publication No. 20977/74.

The silver halide emulsion which can be used in this invention can be suitably selected from various kinds of photographic emulsions depending on the end-use purposes of the photographic materials. Suitable silver halides which can be used in this invention are silver chloride, silver chlorobromide, silver bromide, silver iodobromide, and silver chloroiodobromide. Also, suitable binders for the silver halide emulsions which can be used in this invention are gelatin, gelatin derivatives (e.g., the acrylated gelatin as described in U.S. Pat. No. 3,118,766 and the graft gelatin having as the branch component a vinyl monomer such as acrylic acid as described in U.S. Pat. No. 2,831,767), casein, albumin, agar agar, sodium alginate, starch, cellulose derivatives (e.g., carboxymethyl cellulsoe and hydroxyethyl cellulose), vinyl alcohol, vinylpyrrolidone, polyacrylamide, and the like.

The silver halide emulsions used in this invention can be prepared, e.g., by a single jet method, a double jet method, a control double jet method, and the halogen conversion method as described in British Pat. No. 635,841 and U.S. Pat. No. 3,622,318.

The silver halide emulsion used in this invention can be sensitized by the natural sensitizers present in gelatin, by a sulfur sensitizer, by a reductive sensitizer, and by a noble metal salt using conventional techniques.

The silver halide emulsion can contain an antifogging agent or a stabilizer such as 1-phenyl-5-mercaptotetrazole, 5-methyl-7-hydroxy-1,3,4,7a-tetraazaindene, etc. Also, the silver halide emulsion can contain a sensitizing dye such as a cyanine dye, a merocyanine dye, etc. The silver halide emulsion can contain a coating aid such as saponin, polyethyleneglycol monolauryl ether, etc. Furthermore, the silver halide emulsion can contain a thickener such as polystyrenesulfonic acid, etc., an ultraviolet absorber such as 2-(2-hydroxy-3,5-di-sec-butylphenyl)-5-methoxybenzotriazole, 4-methoxy-α-cyanocinnamic acid-n-dodecyl ester, etc., an antioxidant or a reducing agent such as sodium bisulfite, ascorbic acid, aminophenols, pyrogallols, gallic acids, catechols, resorcinols, and dihydroxynaphthalenes, and an irradiation preventing dye such as an oxonol dye and a styryl dye, and other conventional photographic additives, if desired.

The photographic light-sensitive material of the present invention comprises a support having thereon a silver halide emulsion layer containing a magenta coupler in accordance with the present invention. One preferred embodiment of this photographic light-sensitive material of the present invention comprises a multi-layered, multicolored photographic light-sensitive material comprising a support having thereon a blue-sensitive silver halide emulsion layer containing a yellow color forming coupler, a green-sensitive silver halide emulsion layer containing a magenta color forming coupler in accordance with the present invention, and a red-sensitive silver halide emulsion layer containing a cyan color forming coupler. Known blue-sensitive silver halide emulsions and the red-sensitive silver halide emulsions can be appropriately used. Open-chain type ketomethylene compounds represented by benzoylacetanilides and pivaloylacetanilides can advantageously be used as yellow color forming couplers. Phenolic or naphtholic compounds can advantageously be used as cyan color forming couplers. These color forming couplers can contain a coupling off group on the carbon atom of the coupling position. These color forming couplers are desirably non-diffusible.

The photographic light-sensitive material of the present invention can have, in addition to the aforesaid silver halide emulsion layers, light-insensitive auxiliary layers such as a protective layer, a filter layer, intermediate layers, an antihalation layer, and a backing layer.

The hydrophilic polymer material, particularly gelatin, constituting the layers of the photographic light-sensitive material of the present invention can be hardened by various cross-linking agents. For example, although an inorganic compound such as a chromium salt and a zirconium salt, and an aldehyde type cross-linking agent such as mucochloric acid, 2-phenoxy-3-chloromalealdehydic acid, etc., as described in Japanese patent publication No. 1872/71 can be used, a non-aldehyde type cross-linking agent, for example, a polyepoxy compound as described in Japanese patent publication No. 7133/59, a poly(1-aziridinyl) compound as described in Japanese patent publication No. 8790/62, an active halogen compound as described in U.S. Pat. Nos. 3,362,827 and 3,325,287, etc., are particularly useful.

In the photographic light-sensitive materials of the present invention, any known materials typically used as supports for photographic light-sensitive materials can be suitably used. For instance, preferred examples of such supports are cellulose ester films such as cellulose nitrate films, cellulose acetate films, etc., polyester films such as polyethylene terephthalate films, etc., polyvinyl chloride films, polyvinyl acetal films, polystyrene films, polycarbonate films, polyamide films such as nylon films, baryta-coated papers, α-olefin polymer-coated papers, etc.

The photographic light-sensitive material of the present invention can be suitably used for various purposes such as color positive films, color negative films, color reversal films, color photographic printing papers, etc.

The color photographic light-sensitive material of the present invention provides magenta color images having excellent spectral properties and image fastness when imagewise exposed in a conventional manner and processed using conventional color processing steps. The main color processing steps are color development, bleach, and fix. If desired, wash steps can be inserted between the other steps.

A useful color developer which can be used for developing the color photographic material of this invention is an alkaline aqueous solution containing a color developing agent. Examples of color developing agents which can be used in the color developer include conventional primary aromatic amine color developing agents such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-diethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline), and p-aminophenols (e.g., 4-aminophenol, 2,6-dichloro-4-aminophenol, 2-bromo-4-aminophenol, and 2,6-diiodo-4-aminophenol).

The color developer can contain further conventional additives such as, for instance, an alkali metal sulfite, an alkali metal carbonate, an alkali metal bisulfite, a bromide, an iodide, an alkaline buffer, etc. Furthermore, if desired, the color developer can contain a dye forming coupler, a competitive coupler, an antifoggant, a hardening agent, an antioxidant, a thickener, etc.

The magenta coupler used in the present invention can be converted to an azomethine dye in a high yield through an oxidative coupling reaction wherein exposed silver halide acts as an oxidizing agent. With some conventionally used 4-equivalent couplers, a leuco dye which is an intermediate in dye formation undergoes side reactions with an azine ring or the like being formed, resulting in a low conversion yield to the dye. On the other hand, the magenta couplers used in the present invention can be converted to an azomethine dye in high yield since such a reactive intermediate is substantially not formed due to the presence of a stereochemically bulky substituent at the 3-position of the 5-pyrazolone. As a result, the amount of the magenta forming coupler used in the color light-sensitive material of the present invention can be reduced, which leads to a reduction in silver halide content and in the thickness of an emulsion layer and thus to a reduction of the production cost of the light-sensitive materials, an improvement in the sharpness and facilitating rapid development processing.

The magenta coupler used in the present invention has such a strong coupling activity for an oxidized aromatic primary amine color developing agent that the oxidation product of the developing agent produced upon color development is rapidly removed, thus accelerating the development of the silver halide emulsion.

With the magenta coupler used in the present invention, the process of forming a dye is completed in a color developing bath, which enables the materials to be processed with a bleach-fixing bath containing a weak oxidizing agent such as Fe (III) chelate of ethylenediaminetetraacetic acid (EDTA) or the like and a silver complex salt-forming agent or a ferric salt (e.g., ferric chloride) without using a bleaching bath containing a strong oxidizing agent such as potassium ferricyanide or potassium dichromate. This results in a shortening of the time required for the processing steps of color development and minimizes the problem of environmental pollution due to discharge of processing waste water.

With the magenta coupler used in the present invention, the change in color density is small even when the amount of oil which is used for incorporating the coupler into an emulsion was varied. With most conventionally used magenta couplers, the color density is changed when the amount of the coupler solvent is varied. On the contrary, with the magenta coupler used in the present invention, a degree of the change in the color density is small. As a result, the amount of the high boiling oil which is used as a coupler solvent can be reduced in the color photographic light-sensitive material, which leads to a reduction in the thickness of an emulsion layer and thus to achieving an improvement in image sharpness and facilitating rapid development processing.

The photographic light-sensitive materials of the present invention having the above-described advantages are very useful in the field of color photography.

The present invention will now be illustrated in more detail by reference to the following examples, but the present invention is not to be construed as being limited to these examples. In the examples, the couplers described below were employed as comparison couplers.

Comparison Coupler (A)

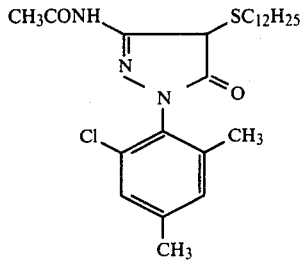

Comparison Coupler (B)

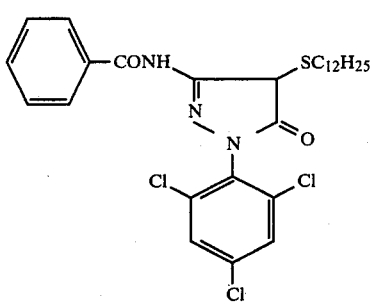

Comparison Coupler (C)

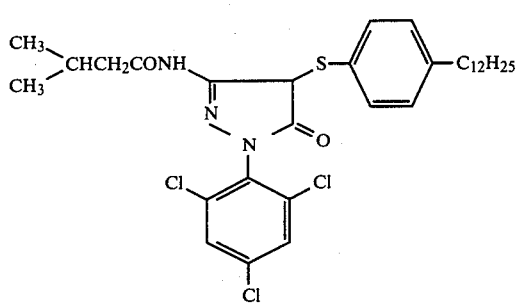

Comparison Coupler (D)

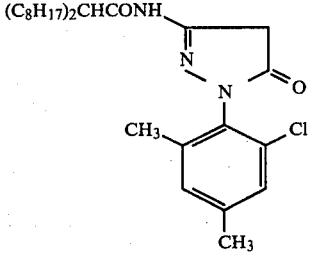

Comparison Coupler (E)

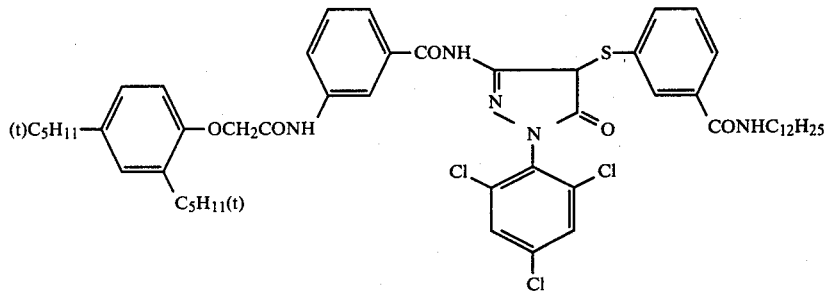

EXAMPLE 1

On a transparent cellulose triacetate film support, an emulsion layer and a protective layer were coated in the order described below to prepare Samples Ia to Xb.

A solution obtained by dissolving 10 g of Coupler (1) according to the present invention in 15 g of tricresyl phosphate and 15 ml of ethyl acetate, which while heating at 60° C. was mixed with 100 ml of an aqueous solution containing 10 g of gelatin, 1 g of sodium dodecylbenzenesulfonate at 50° C. The solution mixture was stirred at high speed using a homogenizer to prepare a fine coupler dispersion. The total amount of the coupler dispersion was added to a mixture of 145 g of silver iodobromide emulsion (molar ratio of silver iodide and silver bromide being 6:94) containing 0.16 mol of silver and 8.7 g of gelatin and 7 ml of a 1% aqueous solution of 6-methyl-4-hydroxy-1,3,3a,7-tetraazaindene, and 9.5 ml of a 2% aqueous solution of 2-hydroxy-4,6-dichloro-s-triazine sodium salt was further added thereto as a hardening agent. The mixture was coated on the above-described support in a coating amount of the coupler of $6 \times 10^{-4}$ mol/m$^2$. On this emulsion layer, a gelatin protective layer was coated in an amount of 0.6 g/m$^2$ to prepare Sample Ia. In the same manner as described in Sample Ia except using 5 g of tricresyl phosphate, a sample was prepared. This is designated Sample Ib.

Using Couplers (3), (6), (8), (10), (20) and (25) according to the present invention, pairs of samples in which the coating amount of coupler (mol/m$^2$) and the mixing ratio of coupler to silver were maintained the same as in Samples Ia and Ib respectively were prepared in an analogous manner to that described above. These samples were designated IIa, IIIb, IIIa, IIIb, IVa, IVb, Va, Vb, VIa, VIb, VIIa and VIIb, respectively.

Furthermore, using Couplers (A), (B) and (C), which are outside of the scope of the present invention, as comparison couplers, pairs of samples were prepared in an analogous manner as described for Samples Ia and Ib. These samples were designated VIIIa, VIIIb, IXa, IXb, Xa and Xb, respectively.

Each of these twenty samples was exposed to light through an optical wedge and then subjected to the following processing steps.

| Processing Step | Temperature (°C.) | Time |
|---|---|---|
| 1. Color Development | 38 | 3 min 15 sec |
| 2. Bleaching | " | 6 min 30 sec |
| 3. Washing with Water | " | 2 min |
| 4. Fixing | " | 4 min |
| 5. Washing with Water | " | 4 min |
| 6. Stabilizing Bath | " | 1 min |

The processing solutions used had the following compositions:

| Color Developer Solution | |
|---|---|
| 4-Amino-N-ethyl-N-(β-methanesulfon-amidoethyl)aniline Monosulfate | 5 g |
| Sodium Sulfite | 5 g |
| Hydroxylamine Sulfate | 2 g |
| Potassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate | 1.2 g |
| to adjust pH to 10.1 | |
| Water to make | 1,000 ml |
| Bleaching Solution | |
| Iron (III) Ammonium Ethylenediamine-tetraacetate | 100 g |
| Disodium Ethylenediaminetetraacetate | 10 g |
| Potassium Bromide | 150 g |
| Glacial Acetic Acid | 10 g |
| Aqueous Ammonia to adjust pH to 6.0 | |
| Water to make | 1,000 ml |
| Fixing Solution | |
| Ammonium Thiosulfate | 150 g |
| Sodium Sulfite | 10 g |
| Sodium Hydrogen Sulfite to adjust pH to 6.0 | 2.5 g |
| Water to make | 1,000 ml |
| Stabilizing Bath | |
| Formalin (37%) | 5 ml |
| Fuji Drywell | 3 ml |
| Water to make | 1,000 ml |

After processing, the optical density to green light of the magenta color image obtained was measured. The results are shown in Table 1 below.

TABLE 1

| Sample No. | Coupler | Fog a | Fog b | Gamma a | Gamma b | Maximum Density a | Maximum Density b | Ratio of Maximum Density b/a |
|---|---|---|---|---|---|---|---|---|
| Ia, b | (1) | 0.04 | 0.04 | 0.47 | 0.43 | 1.63 | 1.56 | 0.96 |
| IIa, b | (3) | 0.05 | 0.05 | 0.54 | 0.52 | 1.81 | 1.78 | 0.98 |
| IIIa, b | (6) | 0.05 | 0.04 | 0.58 | 0.56 | 1.93 | 1.87 | 0.97 |
| IVa, b | (8) | 0.04 | 0.04 | 0.45 | 0.41 | 1.60 | 1.47 | 0.92 |
| Va, b | (10) | 0.04 | 0.04 | 0.46 | 0.41 | 1.61 | 1.48 | 0.92 |
| VIa, b | (20) | 0.04 | 0.04 | 0.47 | 0.43 | 1.65 | 1.53 | 0.93 |
| VIIa, b | (25) | 0.04 | 0.04 | 0.46 | 0.42 | 1.61 | 1.51 | 0.94 |
| VIIIa, b | (A) | 0.04 | 0.04 | 0.40 | 0.24 | 1.44 | 1.01 | 0.70 |
| IXa, b | (B) | 0.05 | 0.04 | 0.56 | 0.41 | 1.88 | 1.42 | 0.75 |
| Xa, b | (C) | 0.04 | 0.04 | 0.47 | 0.33 | 1.65 | 1.20 | 0.73 |

In Table 1, the ratio of maximum color forming density for the samples with respect to which the amount of solvent (tricresyl phosphate) for dispersing coupler was changed is shown as the ratio of maximum density b/a.

It is apparent from the results shown in Table 1 that the magenta couplers according to the present invention exhibit a large value with respect to the ratio of maximum density b/a, and provide a high color forming density in comparison with the comparison couplers even when the amount of the solvent is reduced. This means that the coating amount of coupler or the coating amount of silver can be reduced when the same color forming density is intended by using the same amount of solvent.

EXAMPLE 2

On a paper support having polyethylene layers on both surfaces thereof, an emulsion layer and a protective layer were coated in the order described below to prepare Sample XIa to XVIb. 10 g of each of Couplers (3), (5), (11) and (18) according to the present invention was mixed with 15 g of tricresyl phosphate, 20 ml of ethyl acetate, and 1 g of sodium di(2-ethylhexyl)-α-sulfosuccinate and dissolved by heating. The resulting solution was mixed with 100 ml of an aqueous solution containing 10 g of gelatin at 50° C. and the mixture was stirred at high speed using a homogenizer to prepare an emulsion dispersion.

To a silver chlorobromide emulsion (molar ratio of silver bromide and silver chloride being 50:50) containing 0.45 mol of silver and 60 g of gelatin per kg of emulsion, a 1% aqueous solution of 6-methyl-4-hydroxy-1,3,3a,7-tetraazaindene was added in a ratio of 220 ml per mol of silver in the emulsion. This emulsion was mixed with the total amount of the emulsion dispersion described above in a molar ratio of silver to coupler of 10/1, and then 16 ml of a 2% aqueous solution of 2-hydroxy-4,6-dichloro-s-triazine sodium salt was added thereto as a hardening agent. The resulting mixture was coated on the above-described paper support in a coating amount of the coupler of $4.8 \times 10^{-4}$ mol/m$^2$. On this emulsion layer, a gelatin protective layer was coated in an amount of 0.6 g/m$^2$ to prepare Samples XIa to XIVa. In the same manner as described for Samples XIa to XIVa, using 5 g of tricresyl phosphate, Samples XIb to XIVb were prepared.

Further, using Couplers (A) and (D) which are out of the scope of the present invention, pairs of samples were prepared in the same manner as described above. The samples were designated Samples XVa, XVIa, XVb and XVIb, respectively.

Each of these samples were exposed stepwise to light and subjected to the following development processing.

| Processing Step | Temperature (°C.) | Time |
|---|---|---|
| 1. Color Development | 33 | 3 min 30 sec |
| 2. Bleach-Fixing | 33 | 1 min 30 sec |
| 3. Washing with Water | 25 to 30 | 2 min 30 sec |

The processing solutions used had the following compositions:

| Color Development Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 |
| 4-Amino-N—ethyl-N—(β-methanesulfon-amidoethyl)-m-toluidine Sesquisulfate Monohydrate | 5 g |
| Water to make | 1,000 ml (pH 10.20) |
| Bleach-Fixing Solution | |

-continued

| | |
|---|---|
| Ethylenediaminetetraacetic Acid | 2 g |
| Ferric Salt of Ethylenediamine-tetraacetate | 40 g |
| Sodium Sulfite | 5 g |
| Ammonium Thiosulfate | 70 g |
| Water to make | 1,000 ml |

After processing, the reflective optical density to green light of the magenta color image obtained was measured. The results are shown in Table 2 below.

TABLE 2

| Sample No. | Coupler | Gamma a | Gamma b | Ratio of Gamma b/a | Maximum Density a | Maximum Density b | Ratio of Maximum Density b/a |
|---|---|---|---|---|---|---|---|
| XIa, b | (3) | 1.52 | 1.46 | 0.96 | 1.90 | 1.86 | 0.98 |
| XIIa, b | (5) | 1.42 | 1.35 | 0.95 | 1.79 | 1.72 | 0.96 |
| XIIIa, b | (11) | 1.00 | 0.95 | 0.95 | 1.26 | 1.21 | 0.96 |
| XIVa, b | (18) | 1.42 | 1.32 | 0.93 | 1.83 | 1.68 | 0.92 |
| XVa, b | (A) | 0.90 | 0.60 | 0.67 | 1.13 | 0.87 | 0.77 |
| XVIa, b | (D) | 1.38 | 0.57 | 0.41 | 1.74 | 1.27 | 0.73 |

In Table 2, the ratio of gamma and the ratio of color forming density with the samples in which the amount of solvent (tricresyl phosphate) for dispersing coupler is changed are shown as the ratio of gamma b/a and the ratio of maximum densiby b/a, respectively.

It is apparent from the results shown in Table 2 that the magenta couplers according to the present invention exhibit little change in color forming properties, a high ratio of gamma, and a high ratio of maximum density in comparison with the comparison couplers, when the amount of the solvent was changed.

EXAMPLE 3

On a transparent cellulose triacetate film support, an emulsion layer and a protective layer were coated in the order described below to prepare Samples XVIIa to XXb.

10 g of each of Couplers (6), (12) and (18) according to the present invention was mixed with 15 g of tricresyl phosphate, 20 ml of ethyl acetate and 1 g of sodium di(2-ethylhexyl)-α-sulfosuccinate and dissolved by heating. The resulting solution was mixed with 100 ml of an aqueous solution containing 10 g of gelatin at 50° C. and the mixture was stirred at high speed, using a homogenizer, to prepare an emulsion dispersion.

To a silver iodobromide emulsion (wherein the molar ratio of silver iodide to silver bromide was 2.5/97.5) containing 1.1 mols of silver and 60 g of gelatin per kg of the emulsion, a 1% aqueous solution of 6-methyl-4-hydroxy-1,3,3a,7-tetraazaindene was added in the ratio of 150 ml per mol of silver in the emulsion. This emulsion was mixed with the total amount of the emulsion dispersion described above in a molar ratio of silver to coupler of 8/1, and then 16 ml of a 2% aqueous solution of 2-hydroxy-4,6-dichloro-s-triazine sodium salt was added thereto. The resulting mixture was coated on the above-described support in a coating amount for the coupler of $1 \times 10^{-3}$ mol/m². On this emulsion layer, a gelatin protective layer was coated in an amount of 0.6 g/m² to prepare Samples XVIIa to XIXa. In the same manner as described in Samples XVIIa to XIXa, using 5 g of tricresyl phosphate, Samples XVIIb to XIXb were prepared. Further, using Coupler (B) which is outside of the scope of the present invention, a pair of samples were prepared in the same manner as described above and these were designated as Samples XXa and XXb, respectively.

Each of these samples were exposed to light through an optical wedge, and then subjected to the following processing steps.

| | Processing Step | Temperature (°C.) | Time (minutes) |
|---|---|---|---|
| 1. | First Development | 38 | 3 |
| 2. | Washing with water | " | 1 |
| 3. | Reversal | " | 2 |
| 4. | Color Development | " | 6 |
| 5. | Control | " | 2 |
| 6. | Bleaching | " | 6 |
| 7. | Fixing | " | 4 |
| 8. | Washing with Water | " | 4 |
| 9. | Stabilizing | " | 1 |
| 10. | Drying | " | |

The processing solutions used had the following compositions:

| | |
|---|---|
| First Development Solution | |
| Water | 800 ml |
| Sodium Tetrapolyphosphate | 2.0 g |
| Sodium Hydrogen Sulfite | 8.0 g |
| Sodium Sulfite | 37.0 g |
| 1-Phenyl-3-pyrazolidone | 0.35 g |
| Hydroquinone | 5.5 g |
| Sodium Carbonate Monohydrate | 28.0 g |
| Potassium Bromide | 1.5 g |
| Potassium Iodide | 13.0 mg |
| Sodium Thiocyanate | 1.4 g |
| Water to make | 1,000 ml |
| Reversal Solution | |
| Water | 800 ml |
| Hexasodium Nitrilo—N,N,N—trimethylene Phosphonic Acid | 3.0 g |
| Stannous Chloride Dihydrate | 1.0 g |
| Sodium Hydroxide | 8.0 g |
| Glacial Acetic Acid | 15.0 ml |
| Water to make | 1,000 ml |
| Color Development Solution | |
| Water | 800 ml |
| Sodium Tetrapolyphosphate | 2.0 g |
| Benzyl Alcohol | 5.0 ml |
| Sodium Sulfite | 7.5 g |
| Trisodium Phosphate (12 hydrate) | 36.0 g |
| Potassium Bromide | 1.0 g |
| Potassium Iodide | 90.0 mg |
| Sodium Hydroxide | 3.0 g |
| Citrazic Acid | 1.5 g |
| 4-Amino-3-methyl-N—ethyl-N—(β-hydroxyethyl)aniline Sesquisulfate Monohydrate | 11.0 g |
| Ethylenediamine | 3.0 g |
| Water to make | 1,000 ml |
| Control Solution | |
| Water | 800 ml |
| Glacial Acetic Acid | 5.0 ml |
| Sodium Hydroxide | 3.0 g |
| Dimethylaminoethaneisothiourea Dihydrochloride | 1.0 g |
| Water to make | 1,000 ml |
| Bleaching Solution | |
| Water | 800 ml |
| Sodium Ethylenediaminetetraacetate Dihydrate | 2.0 g |
| Ammonium Iron (III) Ethylenediamine-tetraacetate Dihydrate | 120.0 g |
| Potassium Bromide | 100.0 g |
| Water to make | 1,000 ml |
| Fixing Solution | |
| Water | 800 ml |
| Ammonium Thiosulfate | 80.0 g |
| Sodium Sulfite | 5.0 g |
| Sodium Hydrogen Sulfite | 5.0 g |

-continued

| | |
|---|---|
| Water to make | 1,000 ml |
| Stabilizing Bath | |
| Water | 800 ml |
| Formalin (37%) | 5.0 ml |
| Fuji Drywell | 5.0 ml |
| Water to make | 1,000 ml |

After processing, the optical density to green light of the magenta color image obtained was measured. The results are shown in Table 3 below.

TABLE 3

| Sample No. | Coupler | Gamma a | Gamma b | Maximum Density a | Maximum Density b | Ratio of Maximum Density b/a |
|---|---|---|---|---|---|---|
| XVIIa, b | (6) | 1.50 | 1.39 | 3.16 | 2.91 | 0.92 |
| XVIIIa, b | (12) | 1.31 | 1.21 | 2.80 | 2.52 | 0.90 |
| XIXa, b | (18) | 1.31 | 1.17 | 2.70 | 2.46 | 0.91 |
| XXa, b | (B) | 1.19 | 0.70 | 2.51 | 1.91 | 0.76 |

It is apparent from the results shown in Table 3 that the couplers according to the present invention have a small dependency on the amount of the solvent for color formation, and provide a high color forming density.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon at least one silver halide emulsion layer, said photographic material containing a 5-pyrazolone magenta coupler represented by formula (II) or formula (III)

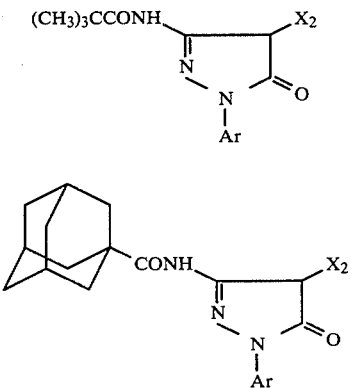

wherein Ar represents a phenyl group which may be substituted with one or more substituents selected from a halogen atom, an alkyl group, an alkoxy group and an acylamino group; and $X_2$ represents an alkylthio or aralkylthio group having from 2 to 30 carbon atoms which may be substituted or an arylthio group having from 6 to 30 carbon atoms which may be substituted.

2. A silver halide color photographic light-sensitive material as in claim 1, wherein said alkyl group present on the phenyl group represented by Ar is a straight chain or branched chain alkyl group having from 1 to 35 carbon atoms.

3. A silver halide color photographic light-sensitive material as in claim 1, wherein said alkoxy group present on the phenyl group represented by Ar is an alkoxy group containing a straight chain or branched chain alkyl group having from 1 to 35 carbon atoms.

4. A silver halide color photographic light-sensitive material as in claim 1, wherein said acylamino group present on the phenyl group represented by Ar is an acylamino group containing a straight chain or branched chain alkyl group having from 1 to 35 carbon atoms.

5. A silver halide color photographic light-sensitive material as in claim 1, wherein $X_2$ represents an alkylthio or aralkylthio group having from 10 to 20 carbon atoms which may be substituted.

6. A silver halide color photographic light-sensitive material as in claim 1, wherein said 5-pyrazolone magenta coupler is diffusion-resistant.

7. A silver halide color photographic light-sensitive material as in claim 1, wherein said 5-pyrazolone magenta coupler is present in a silver halide emulsion layer.

8. A silver halide color photographic light-sensitive material as in claim 7, wherein said 5-pyrazolone magenta coupler is present together with a coupler solvent.

9. A silver halide color photographic light-sensitive material as in claim 8, wherein said coupler solvent is a water-immiscible organic solvent having a melting point of 170° C. or higher.

10. A silver halide color photographic light-sensitive material as in claim 7, wherein said silver halide emulsion layer is a green-sensitive silver halide emulsion layer.

11. A silver halide color photographic light-sensitive material as in claim 1, wherein said magenta coupler is present in a green-sensitive silver halide emulsion layer, wherein said support bears a blue-sensitive silver halide emulsion layer containing a yellow color forming coupler and a red-sensitive silver halide emulsion layer containing a cyan color forming coupler.

12. A silver halide color photographic light-sensitive material as in claim 11, wherein said yellow color forming coupler is an open-chain type ketomethylene compound.

13. A silver halide color photographic light-sensitive material as in claim 11, wherein said cyan color forming coupler is a phenolic compound or a naphthalic compound.

14. A silver halide color photographic light-sensitive material as in claim 11, wherein said yellow, magenta and cyan color forming couplers are non-diffusible.

15. A silver halide color photographic light-sensitive material as in claim 1 or 11 wherein the coupler is coated at a coverage of from about $1 \times 10^{-4}$ to $5 \times 10^{-3}$ mol/m².

16. A silver halide color photographic light-sensitive material as in claim 1 or 11 wherein the coupler is coated at a coverage of from about $3 \times 10^{-4}$ to $2 \times 10^{-3}$ mol/m².

* * * * *